Figure 1:
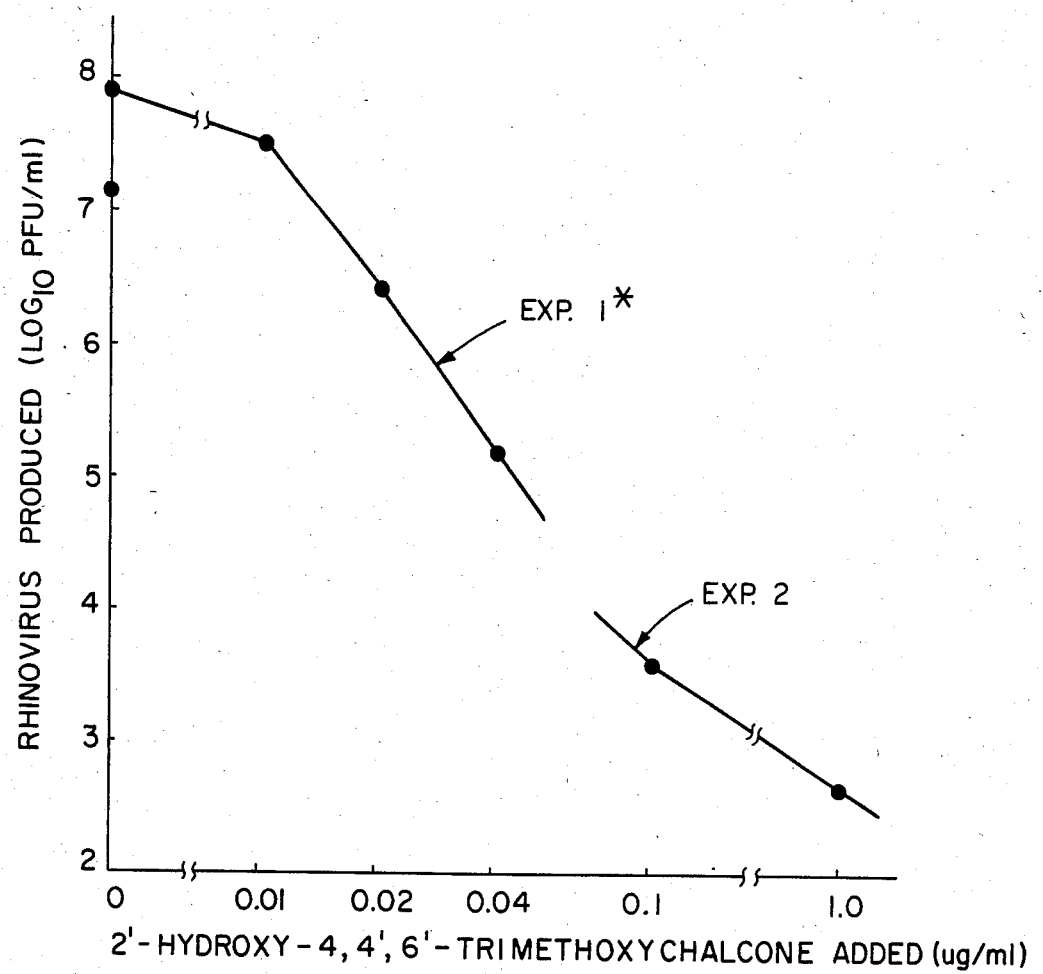

United States Patent [19]

Fujiu et al.

[11] Patent Number: 4,605,674
[45] Date of Patent: Aug. 12, 1986

[54] SUBSTITUTED ACETOPHENONES AND COMPOSITIONS CONTAINING THEM

[75] Inventors: Morio Fujiu, Fujisawa; Yasuji Suhara; Hideo Ishitsuka, both of Yokohama, all of Japan

[73] Assignee: Hoffmann-La Roche Inc., Nutley, N.J.

[21] Appl. No.: 602,633

[22] Filed: Apr. 24, 1984

Related U.S. Application Data

[63] Continuation of Ser. No. 276,578, Jun. 23, 1981, abandoned, which is a continuation of Ser. No. 114,524, Jan. 23, 1980, abandoned.

[30] Foreign Application Priority Data

Jan. 26, 1979 [GB] United Kingdom ............ 7902907

[51] Int. Cl.$^4$ ............ A61K 31/38; A61K 31/34
[52] U.S. Cl. .................. 514/685; 514/277;
514/357; 514/438; 514/461; 514/471; 514/427;
514/456; 514/478; 514/520; 514/523; 514/545;
514/646; 514/676
[58] Field of Search ............ 568/334; 542/438, 440;
514/277, 357, 438, 461, 471, 427, 456, 478, 520,
523, 545, 646, 676, 685

[56] References Cited

U.S. PATENT DOCUMENTS 3,928,421 12/1975 Kyogoku et al.
4,279,930 7/1981 Hall .................... 568/334

FOREIGN PATENT DOCUMENTS 520288 10/1979 Australia.
50-140430 11/1975 Japan .................... 568/334

OTHER PUBLICATIONS

Houben-Weyl, Methoden der Org. Chemie, 1976, vol. 7, pp. 1482–1491.
Beilstein, Handbuch der Org. Chemie, 1925, vol. 8, pp. 432, 433, 501–508, 543, 545.
Beilstein, Handbuch der Org. Chemie, 1931, vol. 8, pp. 707, 708, 738, 739.
Beilstein, Handbuch der Org. Chemie, 1948, vol. 8, pp. 378, 481, 579.

(List continued on next page.)

Primary Examiner—Alan Siegel
Attorney, Agent, or Firm—Jon S. Saxe; Bernard S. Leon; George W. Johnston

[57] ABSTRACT

Antivirally active compounds of the formula

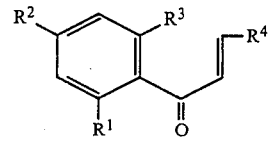

wherein
$R^1$ represents hydroxy, acyloxy derived from an aliphatic acid having 2–18 carbon atoms or a heterocyclic carboxylic acid containing nitrogen atom(s), lower alkoxycarbonyloxy, aminoacyloxy or carboxyalkanoyloxy;
$R^2$ represents lower alkoxy;
$R^3$ represents hydrogen or lower alkoxy; and
$R^4$ represents phenyl which may be substituted by one or more substituents selected from the group consisting of lower alkyl, lower alkoxy, benzyloxy, allyloxy, alkylthio, dialkylamino, amino, cyano, hydroxy, halo and alkylenedioxy; or pyridyl, furyl, thienyl or pyrrolyl which may be substituted by lower alkyl, pharmaceutical compositions containing them and a process for the preparation of those compounds of formula I which are novel.

15 Claims, 2 Drawing Figures

OTHER PUBLICATIONS

Beilstein, Handbuch der Org. Chemie, 1970, vol. 8, p. 2833, 3713, 4114, 4115, 4261.
Beilstein, Handbuch der Org. Chemie, 1944, vol. 8, pp. 547–548.
Beilstein, Handbuch der Org. Chemie, 1967, vol. 8, 4105, 4106, 4262, 4263.
Chem. Abst. 48:1352e (1954).
Chem. Abst. 48:2698g (1954).
Chem. Abst. 64:685c (1966).
Chem. Abst. 85:57378p (1976).
Chem. Abst. 87, 39055t (1977).
Archiv der Pharmazie 292./64.Bd., 1959, Nr. 12, p. 794.
J. Chem. Soc. 1955, p. 171.
Chem. Abstract 44 1494f, 1949.
Chem. Abstract 63 4201C, 1965.
Organic Chemistry 46 1952.
Chem. Abstract 54 1960, 4553g.
Phytochemixtry, 1971, 10, p. 844.
Indian Journal of Chemistry, vol. 7, 1969, p. 1093.
Chem. Abstract 55, 1961, 2271b.
Chem. Abstract 44, 1948, 1493g.
Chem. Abstract 83, 1975, 96950x.
Plant Biochem. 81, 1974, 148520r.
Chem. Abstract 87, 1977, 130461h.
Ann. Chim. (Rome) 50, 202–19 (1960).
Chem. Abstract 66:104929p (1967).
Chem. Abstract 79:53138p (1973).
Chem. Abstract 71:3221z (1969).
Chem. Abstract 81:148530r (1974).
Chem. Abstract 82:111915q (1975).
Chem. Abstract 92:211776v (1980).

SUBSTITUTED ACETOPHENONES AND COMPOSITIONS CONTAINING THEM

This is a continuation of U.S. application Ser. No. 276,578, filed June 23, 1981, now abandoned, which in turn is a continuation of U.S. application Ser. No. 114,524, filed Jan. 23, 1980, now abandoned.

The present invention relates to novel substituted acetophenones, a process for the preparation thereof and antiviral agents containing the novel acetophenones or a known acetophenone.

More particularly, the present invention relates to antiviral agents containing a substituted acetophenone represented by the formula

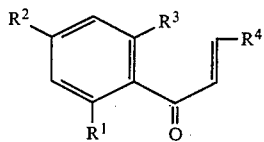
I wherein
$R^1$ represents hydroxy, acyloxy derived from an aliphatic acid having 2–18 carbon atoms or a heterocyclic carboxylic acid containing nitrogen atom(s), lower alkoxycarbonyloxy, aminoacyloxy or carboxyalkanoyloxy;
$R^2$ represents lower alkoxy;
$R^3$ represents hydrogen or lower alkoxy; and
$R^4$ represents phenyl which may be substituted by one or more substituents selected from the group consisting of lower alkyl, lower alkoxy, benzyloxy, allyloxy, alkylthio, dialkylamino, amino, cyano, hydroxy, halo and alkylenedioxy; or pyridyl, furyl, thienyl or pyrrolyl which may be substituted by lower alkyl.

The present invention also relates to the novel substituted acetophenones of the general formula

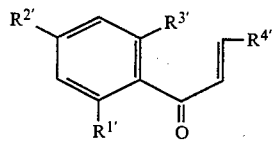
II wherein
$R^{1'}$ represents hydroxy, acyloxy derived from an aliphatic acid having 2–18 carbon atoms or a heterocyclic carboxylic acid containing nitrogen atom(s), lower alkoxycarbonyloxy, aminoacyloxy or carboxyalkanoyloxy;
$R^{2'}$ represents lower alkoxy;
$R^{3'}$ represents lower alkoxy; and
$R^{4'}$ represents phenyl which is substituted by one or more substituents selected from the group consisting of lower alkyl, lower alkoxy, benzyloxy, allyloxy, alkylthio, dialkylamino, amino and cyano; lower alkyl-substituted furyl or pyridyl, thienyl or pyrrolyl which may be substituted by lower alkyl, with the proviso that when $R^{4'}$ is p-methoxyphenyl, $R^{1'}$ is a radical other than acetoxy,
which are useful as effective ingredients of said antiviral agents.

Especially preferred acyloxy groups derived from an aliphatic acid having 2–18 carbons or a heterocyclic carboxylic acid containing nitrogen atom(s) are acetoxy, propionyloxy, butyryloxy, isobutyryloxy, pivaloyloxy, stearoyloxy, nicotinoyloxy, pyrazinylcarbonyloxy and the like. A lower alkoxycarbonyloxy group may contain up to 7 carbon atoms; a preferred group is ethoxycarbonyloxy. An aminoacyloxy group can be derived from an aliphatic amino acid. Especially preferred aminoacyloxy groups are L-lysyloxy, L-alanyloxy and L-glutaminyloxy. A carboxyalkanoyloxy group can be derived from a dicarboxylic acid; a preferred group is 4-carboxybutanoyloxy. A lower alkoxy group contains from 1 to 4 carbon atoms, examples of such groups an methoxy, ethoxy, propoxy and isopropoxy. Preferred substituted phenyl radicals are p-tolyl, p-methoxyphenyl, p-ethoxyphenyl, p-propoxyphenyl, p-(benzyloxy)-m-methoxyphenyl, p-(allyloxy)-phenyl, p-(methylthio)-phenyl, p-(dimethylamino)-phenyl, p-(diethylamino)-phenyl, p-aminophenyl, p-cyanophenyl, p-hydroxyphenyl, p-hydroxy-m-methoxyphenyl, m,p-(methylenedioxy)-phenyl and p-chlorophenyl. Preferred examples of pyridyl, furyl, thienyl or pyrrolyl groups which may be substituted by lower alkyl are 3-pyridyl, 2-furyl, 5-methyl-2-furyl, 2-thienyl, 3-methyl-2-thienyl and 1-methyl-pyrrol-2-yl.

Representative of the compounds defined by formula I which are active as antiviral agents are:
(A) Novel compounds (chalcone=benzylidene acetophenone)

4-(benzyloxy)-2'-hydroxy-3,4',6'-trimethoxychalcone;
4-ethoxy-2'-hydroxy-4',6'-dimethoxychalcone;
2'-hydroxy-4,',6'-dimethoxy-4-propoxychalcone;
2'-hydroxy-4',6'-dimethoxy-4-methylchalcone;
2'-hydroxy-4',6'-dimethoxy-3-(3-pyridyl)-acrylophenone;
2'-hydroxy-4',6'-dimethoxy-3-(methylthio)-chalcone;
4-(allyloxy)-2'-hydroxy-4',6'-dimethoxychalcone;
4-(dimethylamino)-2'-hydroxy-4',6'-dimethoxychalcone;
4-(diethylamino)-2'-hydroxy-4',6'-dimethoxychalcone;
2',4,4'-triethoxy-6'-hydroxychalcone;
2'-hydroxy-4,4'-dimethoxy-6'-propoxychalcone;
2'-hydroxy-6'-isopropoxy-4,4'-dimethoxychalcone;
2'-ethoxy-6'-hydroxy-4,4'-dimethoxychalcone;
2'-hydroxy-4',6'-dimethoxy-3-(2-thienyl)-acrylophenone;
2'-hydroxy-4',6'-dimethoxy-3-(3-methyl-2-thienyl)acrylophenone;
2'-hydroxy-4',6'-dimethoxy-3-(5-methyl-2-furyl)acrylophenone;
2'-hydroxy-4',6'-dimethoxy-3-(N-methyl-2-pyrrolyl)acrylophenone;
4-amino-2'-hydroxy-4',6'-dimethoxychalcone;
4-cyano-2'-hydroxy-4',6'-dimethoxychalcone;
2',4,4'-trimethoxy-6'-(propionyloxy)-chalcone;
2',4,4'-trimethoxy-6'-(octadecanoyloxy)-chalcone;
2'-(ethoxycarbonyloxy)-4,4',6'-trimethoxychalcone;
2',4,4'-trimethoxy-6'-(nicotinoyloxy)-chalcone;
2',4,4'-trimethoxy-6'-(pyrazinylcarbonyloxy)-chalcone;
2'-(L-alanyloxy)-4,4',6'-trimethoxychalcone;
2'-(4-carboxybutanoyloxy)-4,4',6'-trimethoxychalcone;
4-ethoxy-2',4'-dimethoxy-6'-(propionyloxy)-chalcone;
2',4'-dimethoxy-6'-(propionyloxy)-4-propoxychalcone;

2',4'-dimethoxy-4-methyl-6'-(propionyloxy)-chalcone;
2',4'-dimethoxy-4-(methylthio)-6'-(propionyloxy)-chalcone;
4-(allyloxy)-2',4'-dimethoxy-6'-(propionyloxy)-chalcone;
2',4,4'-triethoxy-6'-(propionyloxy)-chalcone;
2',4'-dimethoxy-6'-(propionyloxy)-chalcone;
4-chloro-2',4'-dimethoxy-6'-(propionyloxy)-chalcone;
2'-ethoxy-4,4'-dimethoxy-6'-(propionyloxy)-chalcone;
2',4'-dimethoxy-6'-(propionyloxy)-3-(2-thienyl)-acrylophenone;
2',4'-dimethoxy-3-(5-methyl-2-furyl)-6'-(propionyloxy)-acrylophenone;
2',4'-dimethoxy-3-(1-methylpyrrol-2-yl)-6'-(propionyloxy)-acrylophenone;
3-(2-furyl)-2',4'-dimethoxy-6'-(propionyloxy)-acrylophenone;
2',4'-dimethoxy-3,4-(methylenedioxy)-6'-(propionyloxy)-chalcone;
4,4'-dimethoxy-2'-(propionyloxy)-6'-propoxychalcone;
2'-isopropoxy-4,4'-dimethoxy-6'-(propionyloxy)-chalcone;
4'-ethoxy-2'-hydroxy-4,6'-dimethoxychalcone;
4,4'-diethoxy-2'-hydroxy-6'-methoxychalcone;
2'-hydroxy-3,4',6'-trimethoxychalcone;
2',4'-diethoxy-6'-hydroxy-4'-methoxychalcone;
2'-hydroxy-3,4',5,6'-tetramethoxychalcone;
2,2'-dihydroxy-3,4',6'-trimethoxychalcone;
4'-ethoxy-2'-hydroxy-6'-methoxy-3-(5-methyl-2-furyl)-acrylophenone;
2'-ethoxy-6'-hydroxy-4'-methoxy-3-(5-methyl-2-furyl)-acrylophenone;
2',4'-diethoxy-6'-hydroxy-3-(5-methyl-2-furyl)-acrylophenone;
2',4,4'-trimethoxy-6'-(pivaloyloxy)-chalcone.

(B) Known compounds
2'-hydroxy-4,4',6'-trimethoxychalcone;
2',4'-dihydroxy-4',6'-dimethoxychalcone;
2',4'-dihydroxy-3,4',6'-trimethoxychalcone;
2'-hydroxy-4',6'-dimethoxychalcone;
2'-hydroxy-4',6'-dimethoxy-3,4-(methylenedioxy)-chalcone;
4-chloro-2'-hydroxy-4',6'-dimethoxychalcone;
2'-hydroxy-4,4'-dimethoxychalcone;
3-(2-furyl)-2'-hydroxy-4',6'-dimethoxyacrylophenone;
2'-acetoxy-4,4',6'-trimethoxychalcone;
2',4'-diethoxy-6'-hydroxy-4-methoxychalcone;
2',3'-dihydroxy-4,4',6'-trimethoxychalcone;
2'-hydroxy-3,4,4',6'-tetramethoxychalcone;
2'-hydroxy-2,4,4',6'-tetramethoxychalcone;
2'-hydroxy-2,3,4',6'-tetramethoxychalcone.

According to the process provided by the present invention, the novel substituted acetophenones of formula II hereinbefore are manufactured by (a) reacting a compound of the formula

III wherein $R^{2'}$ and $R^{3'}$ are as defined in formula II, with an aldehyde of formula $$R^{4'}-CHO \qquad IV$$

wherein $R^{4'}$ is as defined in formula II, in an organic solvent in the presence of a basic catalyst, or (b) reacting a compound of the formula

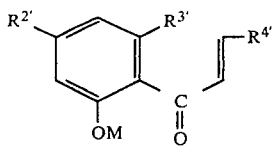

V wherein $R^{2'}$, $R^{3'}$ and $R^{4'}$ are as defined in formula II, and M represents a hydrogen atom or an alkali metal, with an acid anhydride or an acid halide derived from an aliphatic mono- or dicarboxylic acid having 2-18 carbon atoms, a heterocyclic carboxylic acid containing nitrogen atom(s) or an amino acid in an organic solvent.

The reaction in accordance with embodiment (a) of said process can be carried out by adding a basic catalyst, for example, an alkali metal hydroxide or carbonate such as sodium hydroxide, potassium hydroxide, sodium carbonate or potassium carbonate; or an alcoholate, such as sodium ethoxide or potassium ethoxide, to a mixture of compounds of formulae III and IV in an organic solvent, such as methanol, ethanol, dioxane, tetrahydrofuran, benzene or hexane, and stirring the mixture for several hours to 5 days at 0°–100° C. The desired compound of formula II can be isolated from the reaction mixture and purified by known methods, e.g. by recrystallization, chromatography and the like. When the compound of formula IV contains an amino group, this group should be protected by conversion into a suitable protected amino group such as acetamido, prior to the reaction.

The reaction in accordance with embodiment (b) of said process can be carried out in an organic solvent, such as pyridine, dimethylaminopyridine, lutidine or triethylamine at a temperature of 0° to 80° C. for 1–10 hours. Preferred examples of acid anhydrides or acid halides are stearic anhydride, gluatric anhydride; acetyl chloride, propionyl chloride, ethyl chloroformate, nicotinoyl chloride, pyrazinylcarbonyl chloride or halides of amino acids. In said reaction, an aliphatic mono- or dicarboxylic acid having 2-18 carbon atoms, a heterocyclic carboxylic acid containing nitrogen atom(s), or an amino acid in a form of a free acid may be used together with a reagent which is capable of converting said acid into the corresponding halide in the reaction medium. Examples of preferred reagents are thionyl chloride and thionyl bromide. When an amino acid or a halide thereof is used in said reaction, the amino group should be protected by conversion into a suitable protected amino group such as benzyloxycarbonyl amino. The protecting group can be readily removed by a method known per se after the completion of the reaction.

The substituted acetophenones of formula I and formula II provided by the present invention exhibit an antiviral activity and especially inhibit the replication of human rhinoviruses in human embryonic lung cell or HeLa cell cultures at concentration of 0.006-1 μg/ml.

Results of antiviral activity studies:
1. In vitro antiviraL activity (A) Inhibition of viral cytopathogenic effect:

A suspension of HeLa cells ($6 \times 10^4$) was mixed with rhinovirus HGP ($3 \times 10^3$ plaque forming units, PFU) and was plated in a microtest plate containing the compounds to be tested serially diluted. The cells were then cultured with Eagle's minimum essential medium containing 2% calf serum, 1% tryptose phosphate broth, 100 μg/ml of streptomycin sulfate and 20 unit/ml of penicillin G. Viral c.p.e. (cytopathogenic effect) was observed by a microscope after 2 days culture at 33° C.

The test results are shown in Table 1. The antiviral activity of the tested compounds is expressed by the concentration inhibiting the viral c.p.e. by 50% when compared to the control culture ($IC_{50}$).

TABLE 1

| Compound | $IC_{50}$ (μg/ml) against rhinovirus HGP |
|---|---|
| 2'-hydroxy-4',4',6'-trimethoxychalcone | 0.01 |
| 2',4-dihydroxy-4',6'-dimethoxychalcone | 0.3–1 |
| 4-(benzyloxy)-2'-hydroxy-3,4',6'-trimethoxychalcone | 1 |
| 4-ethoxy-2'-hydroxy-4',6'-dimethoxychalcone | 0.02–0.05 |
| 2',4-dihydroxy-3,4',6'-trimethoxychalcone | 0.3–1 |
| 2'-hydroxy-4',6'-dimethoxy-4-propoxychalcone | 0.1 |
| 2'-hydroxy-4',6'-dimethoxychalcone | 0.1–0.3 |
| 2'-hydroxy-4',6'-dimethoxy-4-methylchalcone | 0.01 |
| 2'-hydroxy-4',6'-dimethoxy-3-(3-pyridyl)-acrylophenone | 0.6 |
| 2'-hydroxy-4',6'-dimethoxy-3,4-(methylenedioxy)-chalcone | 0.02 |
| 2'-hydroxy-4',6'-dimethoxy-4-(methylthio)-chalcone | 0.03 |
| 4-(allyloxy)-2'-hydroxy-4',6'-dimethoxychalcone | 0.03–0.1 |
| 4-(dimethylamino)-2'-hydroxy-4',6'-dimethoxychalcone | 0.02–0.06 |
| 4-(diethylamino)-2'-hydroxy-4',6'-dimethoxychalcone | 0.6–2 |
| 4-chloro-2'-hydroxy-4',6'-dimethoxychalcone | 0.02–0.06 |
| 2',4,4'-triethoxy-6'-hydroxychalcone | 0.25 |
| 2'-hydroxy-4,4'-dimethoxychalcone | 0.3–1 |
| 2'-hydroxy-4,4'-dimethoxy-6'-propoxychalcone | 0.06 |
| 2'-hydroxy-6'-isopropoxy-4,4'-dimethoxychalcone | 0.1–0.2 |
| 2'-ethoxy-6'-hydroxy-4,4'-dimethoxychalcone | 0.01 |
| 3-(2-furyl)-2'-hydroxy-4',6'-dimethoxyacrylphenone | 0.06–0.2 |
| 2'-hydroxy-4',6'-dimethoxy-3-(2-thienyl)-acrylophenone | 0.03 |
| 2'-hydroxy-4',6'-dimethoxy-3-(3-methyl-2-thienyl)acrylophenone | 0.1 |
| 2'-hydroxy-4',6'-dimethoxy-3-(5-methyl-2-furyl)-acrylophenone | 0.03 |
| 2'-hydroxy-4',6'-dimethoxy-3-(N—methyl-2-pyrrolyl)-acrylophenone | 0.1 |
| 4-amino-2'-hydroxy-4',6'-dimethoxychalcone | 0.03–0.1 |
| 4-cyano-2'-hydroxy-4',6'-dimethoxychalcone | 0.3 |
| 2'-acetoxy-4,4',6'-trimethoxychalcone | 0.006 |
| 2',4,4'-trimethoxy-6'-(propionyloxy)-chalcone | 0.01 |
| 2',4,4'-trimethoxy-6'-(octadecanoyloxy)-chalcone | 0.05–0.1 |
| 2'-(ethoxycarbonyloxy)-4,4',6'-trimethoxychalcone | 0.04 |
| 2',4,4'-trimethoxy-6'-(nicotinoyloxy)-chalcone | 0.01–0.025 |
| 2',4,4'-trimethoxy-6'-(pyrazinylcarbonyloxy)-chalcone | 0.03–0.1 |

TABLE 1-continued

| Compound | $IC_{50}$ (μg/ml) against rhinovirus HGP |
|---|---|
| 2'-(L-alanyloxy)-4,4',6'-trimethoxychalcone | 0.03–0.1 |
| 2'-(4-carboxybutanoyloxy)-4,4',6'-trimethoxychalcone | 0.03 |
| 4-ethoxy-2',4'-dimethoxy-6'-(propionyloxy)-chalcone | 0.03–0.1 |
| 2',4'-dimethoxy-6'-(propionyloxy)-4-propoxychalcone | 0.1–0.3 |
| 2',4'-dimethoxy-4-methyl-6'-(propionyloxy)-chalcone | 0.03 |
| 2',4'-dimethoxy-4-(methylthio)-6'-(propionyloxy)-chalcone | 0.03–0.1 |
| 4-(allyloxy)-2',4'-dimethoxy-6'-(propionyloxy)-chalcone | 0.03–0.1 |
| 2',4,4'-triethoxy-6'-(propionyloxy)-chalcone | 0.1–0.3 |
| 2',4'-dimethoxy-6'-(propionyloxy)chalcone | 0.3–1 |
| 4-chloro-2',4'-dimethoxy-6'-(propionyloxy)-chalcone | 0.1–0.3 |
| 2'-ethoxy-4,4'-dimethoxy-6'-(propionyloxy)chalcone | 0.02–0.06 |
| 2',4'-dimethoxy-6'-(propionyloxy)-3-(2-thienyl)-acrylophenone | 0.1–0.3 |
| 2',4'-dimethoxy-3-(5-methyl-2-furyl)-6'-(propionyloxy)-acrylophenone | 0.03–0.1 |
| 2',4'-dimethoxy-3-(1-methylpyrrol-2-yl)-6'-(propionyloxy)-acrylophenone | 0.3 |
| 3-(2-furyl)-2',4'-dimethoxy-6'-(propionyloxy)-acrylophenone | 0.1–0.3 |
| 2',4'-dimethoxy-3,4-(methylenedioxy)-6'-(propionyloxy)-chalcone | 0.1 |
| 4,4'-dimethoxy-2'-(propionyloxy)-6'-propoxychalcone | 0.03–0.1 |
| 2'-isopropoxy-4,4'-dimethoxy-6'-(propionyloxy)-chalcone | 0.01–0.03 |
| 4'-ethoxy-2'-hydroxy-4,6'-dimethoxychalcone | 0.002–0.006 |
| 4,4'-diethoxy-2'-hydroxy-6'-methoxychalcone | 0.006–0.02 |
| 2'-hydroxy-3,4',6'-trimethoxychalcone | 0.1 |
| 2',4-diethoxy-6'-hydroxy-4'-methoxychalcone | 0.1 |
| 2'-hydroxy-3,4',5,6'-tetramethoxychalcone | 0.3 |
| 2,2'-dihydroxy-3,4',6'-trimethoxychalcone | 0.15–0.5 |
| 4'-ethoxy-2'-hydroxy-6'-methoxy-3-(5-methyl-2-furyl)-acrylophenone | 0.03 |
| 2'-ethoxy-6'-hydroxy-4'-methoxy-3-(5-methyl-2-furyl)-acrylophenone | 0.04 |
| 2',4'-diethoxy-6'-hydroxy-3-(5-methyl-2-furyl)-acrylophenone | 0.04–0.12 |
| 2',4,4'-trimethoxy-6'-(pivaloyloxy)-chalcone | 0.01–0.03 |
| 2',4'-diethoxy-6'-hydroxy-4-methoxychalcone | 0.03–0.1 |
| 2',3-dihydroxy-4,4',6'-trimethoxychalcone | 0.1–0.3 |
| 2'-hydroxy-3,4,4',6'-tetramethoxychalcone | 0.1–0.3 |
| 2'-hydroxy-2,4,4',6'-tetramethoxychalcone | 0.1 |
| 2'-hydroxy-2,3,4',6'-tetramethoxychalcone | 0.1 |

(B) Inhibition of viral replication:

Effect of 2'-hydroxy-4,4',6'-trimethoxychalcone on the replication of rhinovirus HGP in HeLa cells was tested. Monolayers of HeLa cells ($4 \times 10^5$) to which 2'-hydroxy-4,4',6'-trimethoxychelcone at various concentrations had been added were infected with rhinovirus HGP ($4 \times 10^4$ PFU) for 60 minutes. Thereafter, the cells were washed with Eagle's minimum essential medium and further cultured with said medium containing 2% calf serum, 1% tryptose phosphate broth, 100 μg/ml of streptomycin sulfate and 20 units/ml of penicillin G. The total yield of the virus replicated in the culture medium was assayed 2 days after infection.

The results are shown in FIG. 1, demonstrating that 2'-hydroxy-4,4',6'-trimethoxy-chalcone reduces the viral replication quite considerably in concentrations of 0.1–1.0 μg/ml, without showing any cytotoxic symptom.

Figure 2:
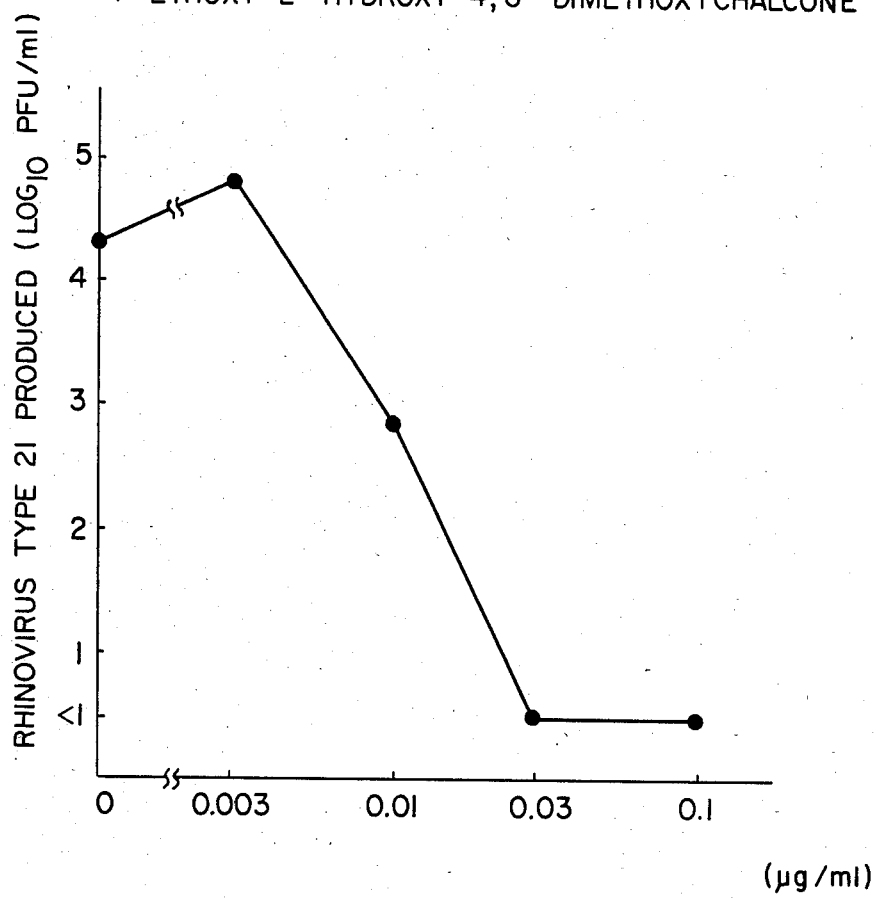

In the same manner the effect of 4'-ethoxy-2'-hydroxy-4,6-dimethoxychalcone on the replication of rhinovirus type 21 in HeLa cells was tested. The results are shown in FIG. 2, demonstrating that 4'-ethoxy-2'-hydroxy-4,6-dimethoxy-chalcone reduces the viral replication very effectively in concentrations of 0.03 μg/ml, without showing any cytotoxic symptom.

2. In vivo antiviral activity

The activity of the compounds against lethal infection with Coxsackievirus B1 was tested in mice. DDY mice weighing about 15 g were infected intraperitoneally with about the tenfold $LD_{50}$ dose of the virus. The infected mice were treated 9 times with the compounds either orally 0, 2, 5, 18, 24, 42, 48, 66 and 72 hours or intraperitoneally 1, 2, 4, 18 and 28 hours after infection. The survivals were recorded up to 21 days.

The results are shown in Table 2. Non-treated (controls) mice died at 3 to 5 days after infection.

TABLE 2

Antiviral activity against Coxsackievirus B1 in mice

| Compound | Dose | route | Survival [%] |
|---|---|---|---|
| 2'-hydroxy-4,4',6'-trimethoxychalcone | 40 mg/kg × 9<br>20 | p.o.<br>p.o. | 60<br>40 |
| 2'-acetoxy-4,4',6'-trimethoxychalcone | 40 mg/kg × 9<br>20 | p.o.<br>p.o. | 70<br>40 |
| 2'-hydroxy-4',6'-dimethoxy-3-(2-thienyl)-acrylophenone | 40 mg/kg × 9<br>20 | p.o.<br>p.o. | 70<br>30 |
| control | — | — | 20 |
| 2'-acetoxy-4,4',6'-trimethoxychalcone | 40 mg/kg × 5 | i.p. | 50 |
| 2',4,4'-trimethoxy-6'-(propionyloxy)chalcone | 40 mg/kg × 5<br>20 | i.p. | 75<br>25 |
| control | — | — | 0 |

In addition to the above, the compounds provided by the present invention are well tolerated and do not show any toxic activity at concentrations which are 10 to 1,000 times higher than their effective dosages against rhinovirus infections. When administered orally the compounds did not show any toxic symptoms at dosages of 5 g/kg or more. The acute toxicity data is summarized in Table 3.

TABLE 3

| Compound | $LD_{50}$ (mg/kg)[1] i.p.[2] | p.o.[3] |
|---|---|---|
| 2'-hydroxy-4,4',6'-trimethoxychalcone | >1,000 | >5,000 |
| 2'-acetoxy-4,4',6'-trimethoxychalcone | >1,000 | >5,000 |
| 4-(dimethylamino)-2'-hydroxy-4',6'-dimethoxychalcone | >1,000 | >5,000 |
| 2'-hydroxy-4',6'-dimethoxy-3-(2-thienyl)acrylophenone | >1,000 | >5,000 |
| 4-chloro-2'-hydroxy-4',6'-dimethoxychalcone | >1,000 | >5,000 |
| 4-ethoxy-2'-hydroxy-4',6'-dimethoxychalcone | >1,000 | >5,000 |
| 2'-hydroxy-4',6'-dimethoxy-4-methylchalcone | >1,000 | >5,000 |
| 2'-hydroxy-4',6'-dimethoxy-3,4-(methylenedioxy)-chalcone | >1,000 | >5,000 |
| 2'-hydroxy-4',6'-dimethoxy-4-(methylthio)chalcone | >1,000 | >5,000 |
| 2'-hydroxy-4',6'-dimethoxy-3-(3-methyl-2-thienyl)-acrylophenone | >500 | >1,500 |
| 2'-hydroxy-4',6'-dimethoxy-3-(5-methyl-2-furyl)-acrylophenone | >500 | >2,000 |
| 2'-hydroxy-4',6'-dimethoxy-3-(N—methyl-2-pyrrolyl)-acrylophenone | >500 | >1,000 |
| 4-cyano-2'-hydroxy-4',6'-dimethoxychalcone | >500 | >1,000 |
| 2',4,4'-trimethoxy-6'-(propionyloxy)chalcone | >500 | >5,000 |
| 2',4,4'-trimethoxy-6'-(octadecanoyloxy)-chalcone | >500 | >4,000 |
| 2'-(ethoxycarbonyloxy)-4,4',6'-trimethoxychalcone | >500 | >4,000 |
| 2',4,4'-trimethoxy-6'-(nicotinoyloxy)-chalcone | >500 | >4,000 |
| 2',4,4'-trimethoxy-6'-(pyrazinylcarbonyloxy)-chalcone | >500 | >4,000 |
| 2'-(L-alanyloxy)-4,4',6'-trimethoxychalcone | >180 | >1,000 |
| 2'-(4-carboxybutanoyloxy)-4,4',6'-trimethoxychalcone | >500 | >2,000 |
| 2',4-dihydroxy-4',6'-dimethoxy-chalcone | >500 | >3,200 |
| 4-(benzyloxy)-2'-hydroxy-3,4',6'-trimethoxychalcone | >500 | >1,500 |
| 2'-hydroxy-4',6'-dimethoxy-4-propoxychalcone | >500 | >5,000 |
| 2'-hydroxy-4',6'-dimethoxychalcone | >1,000 | >5,000 |
| 4-(allyloxy)-2'-hydroxy-4',6'-dimethoxychalcone | >500 | >1,000 |
| 2',4,4'-triethoxy-6'-hydroxychalcone | >1,000 | >3,000 |
| 2'-hydroxy-4,4'-dimethoxychalcone | >1,000 | >2,500 |
| 2'-hydroxy-4,4'-dimethoxy-6'-propoxychalcone | >500 | >1,500 |
| 2'-hydroxy-6'-isopropoxy-4,4'-dimethoxychalcone | >500 | >2,700 |
| 2'-ethoxy-6'-hydroxy-4,4'-dimethoxychalcone | >500 | >1,000 |
| 3-(2-furyl)-2'-hydroxy-4',6'-dimethoxychalcone | >500 | >1,500 |
| 4-ethoxy-2',4'-dimethoxy-6'-(propionyloxy)chalcone | >1,000 | >5,000 |
| 2',4'-dimethoxy-6'-(propionyloxy)-4-propoxychalcone | >1,000 | >5,000 |
| 2',4'-dimethoxy-4-methyl-6'-(propionyloxy)chalcone | >1,000 | >5,000 |
| 2',4'-dimethoxy-4-(methylthio)-6'-(propionyloxy)chalcone | >1,000 | >5,000 |
| 4-(allyloxy)-2',4'-dimethoxy-6'-(propionyloxy)chalcone | >500 | >1,000 |
| 2',4,4'-triethoxy-6'-(propionyloxy)chalcone | >1,000 | >5,000 |
| 2',4'-dimethoxy-6'-(propionyloxy)chalcone | >1,000 | >5,000 |
| 4-chloro-2',4'-dimethoxy-6'-(propionyloxy)chalcone | >1,000 | >5,000 |
| 2'-ethoxy-4,4'-dimethoxy-6'-(propionyloxy)chalcone | >1,000 | >5,000 |
| 2',4'-dimethoxy-6'-(propionyloxy)-3-(2-thienyl)acrylophenone | >1,000 | >5,000 |
| 2',4'-dimethoxy-3-(5-methyl-2-furyl)-6'-(propionyloxy)-acrylophenone | >500 | >2,000 |
| 2',4'-dimethoxy-3-(1-methylpyrrol-2-yl)-6'-(propionyloxy)-acrylophenone | >500 | >5,000 |
| 3-(2-furyl)-2',4'-dimethoxy-6'-(propionyloxy)acrylophenone | >500 | >1,000 |
| 2',4'-dimethoxy-3,4-(methylenedioxy)-6'-(propionyloxy)-chalcone | >500 | >1,000 |
| 4,4'-dimethoxy-2'-(propionyloxy)-6'-propoxychalcone | >500 | >1,000 |
| 2'-isopropoxy-4,4'-dimethoxy- | >500 | >1,000 |

TABLE 3-continued

| Compound | LD$_{50}$ (mg/kg)[1] | |
|---|---|---|
| | i.p.[2] | p.o.[3] |
| 6'-(propionyloxy)-chalcone | | |
| 4'-ethoxy-2'-hydroxy-4,6'-dimethoxychalcone | >1,000 | >5,000 |
| 4,4'-diethoxy-2'-hydroxy-6'-methoxychalcone | >500 | >1,000 |
| 2'-hydroxy-3,4',6'-trimethoxychalcone | >500 | >1,000 |
| 2',4-diethoxy-6'-hydroxy-4'-methoxychalcone | >500 | >5,000 |
| 2'-hydroxy-3,4',5,6'-tetramethoxychalcone | >500 | >5,000 |
| 2,2'-dihydroxy-3,4',6'-trimethoxychalcone | >500 | >1,000 |
| 4'-ethoxy-2'-hydroxy-6'-methoxy-3-(5-methyl-2-furyl)-acrylophenone | >500 | >1,000 |
| 2'-ethoxy-6'-hydroxy-4'-methoxy-3-(5-methyl-2-furyl)-acrylphenone | >500 | >1,000 |
| 2',4'-diethoxy-6'-hydroxy-3-(5-methyl-2-furyl)-acrylphenone | >500 | >1,000 |
| 2',4,4'-trimethoxy-6'-pivaloyloxychalcone | >1,000 | >5,000 |
| 2',4'-diethoxy-6'-hydroxy-4-methoxychalcone | >1,000 | >2,000 |
| 2',3-dihydroxy-4,4',6'-trimethoxychalcone | >500 | >1,000 |
| 2'-hydroxy-3,4,4',6'-tetramethoxychalcone | >500 | >500 |
| 2'-hydroxy-2,4,4',6'-tetramethoxychalcone | >500 | >1,000 |
| 2'-hydroxy-2,3,4',6'-tetramethoxychalcone | >500 | >1,000 |

[1]DDY mice weighing 15-20 g were treated with a single dose of the compound. Survivors were recorded on day 21.
[2]Compounds were dissolved in dimethylsulfoxide.
[3]Compounds were suspended with solution of 0.5% carboxymethyl cellulose.

As mentioned above, the compounds of formula I and formula II can be used as medicaments against viral diseases, especially against common cold, in the form of pharmaceutical preparations.

The pharmaceutical preparations contain at least one of said antiviral compounds in association with a compatible pharmaceutical carrier material and may also contain other pharmaceutically active compounds. The pharmaceutical preparations include a solid form for oral administration such as tablets, capsules, pills, powders and granules; a liquid form for oral administration such as solutions, suspensions, syrups and elixers; preparations for parenteral administration such as sterile solutions, suspensions or emulsions; and preparations for topical administration such as solutions, emulsions, micronized powders, ointments, gargles, troches and aerosoles.

The pharmaceutical preparations can be administered so that the concentration of active ingredient is greater than the minimum inhibitory concentration for particular viral infection being treated.

The dosage for treatment depends up on the route of administration, the age, weight, and the condition of the patient, and the particular disease to be treated. In general, for adults a suggested dosage for use in common cold is about 100 to 2,000 mg, 3 to 6 times daily for an oral treatment, and is about 0.1 to 100 μg/cm$^2$, 3 to 6 times daily for a topical application.

The following Examples illustrate the present invention:

EXAMPLE 1

To a stirred solution containing 196 mg of 2'-hydroxy-4',6'-dimethoxyacetophenone and 150 mg of anisaldehyde in 3 ml of ethanol was added 50% aqueous potassium hydroxide (3 ml). After being stirred at room temperature for 3 days, the mixture was poured into 30 ml of cold water. The mixture was then extracted with three 30 ml portions of ethyl acetate. The combined ethyl acetate extracts were washed with water, dried over anhydrous sodium sulfate and then evaporated under reduced pressure to give a crystalline residue. Recrystallization of the residue from methanol gave 182 mg (50% yield) of 2'-hydroxy-4,4',6'-trimethoxychalcone as yellow needles: m.p. 110.7° C.

EXAMPLE 2

In a manner analogous to that described in Example 1 the following substituted acetophenones were obtained from the corresponding acetophenones and aldehydes:

2',4'-dihydroxy-4',6'-dimethoxychalcone; m.p. 194.7° C. (recrystallized from methanol).

4-(benzyloxy)-2'-hydroxy-3,4',6'-trimethoxychalcone; m.p. 130.7° C. (methanol).

4-ethoxy-2'-hydroxy-4',6'-dimethoxychalcone; m.p. 136.5° C. (methanol).

2',4-dihydroxy-3,4',6'-trimethoxychalcone; m.p. 176.8° C. (methanol).

2'-hydroxy-4',6'-dimethoxy-4-propoxychalcone; m.p. 96.7° C. (methanol).

2'-hydroxy-4',6'-dimethoxychalcone; m.p. 85.5° C. (methanol).

2'-hydroxy-4',6'-dimethoxy-4-methylchalcone; m.p. 129.5° C. (methanol).

2'-hydroxy-4',6'-dimethoxy-3-(3-pyridyl)-acrylophenone; m.p. 158.3° C. (methanol).

2'-hydroxy-4',6'-dimethoxy-3,4-(methylenedioxy)-chalcone; m.p. 161.7° C. (methanol).

2'-hydroxy-4',6'-dimethoxy-4-(methylthio)-chalcone; m.p. 134.6° C. (methanol).

4-(allyloxy)-2'-hydroxy-4',6'-dimethoxychalcone; m.p. 112.3° C. (methanol).

4-(dimethylamino)-2'-hydroxy-4',6'-dimethoxychalcone; m.p. 196.7° C. (methanol).

4-(diethylamino)-2'-hydroxy-4',6'-dimethoxychalcone; m.p. 121.8° C. (ether/petrol ether).

4-chloro-2'-hydroxy-4',6'-dimethoxychalcone; m.p. 167.3° C. (methanol).

2',4,4'-triethoxy-6'-hydroxychalcone; m.p. 131.0° C. (methanol).

2'-hydroxy-4,4'-dimethoxychalcone; m.p. 108.0° C. (ethanol).

2'-hydroxy-4,4'-dimethoxy-6'-propoxychalcone; m.p. 116.7° C. (ethanol).

2'-hydroxy-6'-isopropoxy-4,4'-dimethoxychalcone; m.p. 112.8° C. (ethanol).

2'-ethoxy-6'-hydroxy-4,4'-dimethoxychalcone; m.p. 123.6° C. (methanol).

3-(2-furyl)-2'-hydroxy-4',6'-dimethoxyacrylophenone; m.p. 98.4° C. (methanol).

2'-hydroxy-4',6'-dimethoxy-3-(2-thienyl)-acrylophenone; m.p. 124.4° C. (methanol).

2'-hydroxy-4',6'-dimethoxy-3-(3-methyl-2-thienyl)-acrylophenone; m.p. 124.4° C. (methanol).

2'-hydroxy-4',6'-dimethoxy-3-(5-methyl-2-furyl)-acrylophenone; m.p. 103.1° C. (methanol).

2'-hydroxy-4',6'-dimethoxy-3-(1-methyl-pyrrol-2-yl)-acrylophenone; m.p. 139.8° C. (methanol).

EXAMPLE 3

A mixture of 98 mg of 2'-hydroxy-4',6'-dimethoxyacetophenone, 85 mg of 4-acetamidobenzaldehyde and 1 g of potassium hydroxide in 4 ml of 50% aqueous ethanol was stirred at room temperature for 3 days. The mixture was poured into 30 ml of cold water and then extracted with three 30 ml portions of ethyl acetate. The combined extracts were washed with water, dried over anhydrous sodium sulfate and evaporated under reduced pressure. The residue was purified by preparative thin layer chromatography using a silica gel plate (Kiesel gel 60 F254, Merck Co.) and cyclohexane/ethyl acetate (1:1, v/v) as the developing solvent, whereby 12 mg of 4-amino-2'-hydroxy-4',6'-dimethoxychalcone as a yellow powder were obtained: Rf value 0.22; $^1$H-nmr spectrum (in CDCl$_3$): $\delta$3.6(2H), 3.72(3H), 3.82(3H), 5.90(1H), 6.06(1H), 6.56(1H), 6.70(1H), 7.50(1H), 7.62(1H) and 14.4 ppm (1H).

EXAMPLE 4

To a stirred solution containing 196 mg of 2'-hydroxy-4',6'-dimethoxyacetophenone and ca. 100 mg of freshly prepared sodium ethoxide in 5 ml of absolute ethanol was added 4-cyanobenzaldehyde (131 mg). The mixture was stirred at room temperature for 5 hours. Water (30 ml) was added, the mixture was adjusted to pH 4 with dilute hydrochloric acid and then extracted with three 30 ml portions of ethyl acetate. The combined extracts were washed with water, dried over anhydrous sodium sulfate and then evaporated under reduced pressure to give 108 mg of solid residue. Recrystallization of the residue from methanol yielded 78 mg (25% yield) of yellow crystals, 4-cyano-2'-hydroxy-4',6'-dimethoxychalcone; m.p. 230.9° C.

EXAMPLE 5

To an ice-cooled solution of 300 mg of 2'-hydroxy-4,4',6'-trimethoxychalcone in 5 ml of pyridine was added 0.1 ml of acetyl chloride, and the mixture was stirred at room temperature for 1 hour. After removal of the solvent by evaporation under reduced pressure, the residue was treated with 10 ml of ice-water and 30 ml of chloroform. The mixture was shaken, and the chloroform layer was separated, washed with three 10 ml portions of water, dried over anhydrous sodium sulfate and then evaporated under reduced pressure. The resulting crsytalline residue was recrystallized from ethyl acetate/hexane to give 310 mg (92% yield) of 2'-acetoxy-4,4',6'-trimethoxychalcone as colorless needles; m.p. 105°–107° C.

EXAMPLE 6

A solution of 500 mg of 2'-hydroxy-4,4',6'-trimethoxychalcone and 0.15 ml of propionyl chloride in 5 ml of pyridine was stirred at room temperature for 6 hours. After removal of the solvent, the residue was treated with 10 ml of ice-water and 30 ml of chloroform. The mixture was shaken, and the chloroform layer was separated, washed with three 10 ml portions of water, dried over anhydrous sodium sulfate and then evaporated under reduced pressure. The oily residue was washed with a small amount of hexane, and the resulting solid was crystallized from ethanol/hexane, yielding 530 mg (90% yield) of 2',4,4'-trimethoxy-6'-(propionyloxy)chalcone as pale yellow needles; m.p. 117°–118° C.

EXAMPLE 7

A solution of 2'-hydroxy-4,4',6'-trimethoxychalcone (120 mg) and stearic anhydride (210 mg) in 10 ml of pyridine was stirred at 105° C. for 8 hours and then evaporated. To the oily residue were added 30 ml of ethyl acetate and 30 ml of saturated aqueous sodium bicarbonate, and the mixture was shaken, whereupon a solid of sodium stearate was precipitated. After removal of the precipitate by filtration, the ethylacetate layer was separated, washed with water, dried over Na$_2$SO$_4$ and evaporated. Recrystallization of the residue from methanol gave 200 mg (91% yield) of 2',4,4'-trimethoxy-6'-(octadecanoyloxy)chalcone as pale yellow needles; m.p. 65°–66° C.

EXAMPLE 8

Ethyl chloroformate (216 mg) was added dropwise to a solution of 2'-hydroxy-4,4',6'-trimethoxychalcone (314 mg) in 5 ml of pyridine. After stirring at room temperature for 30 minutes, the mixture was poured into water (30 ml). The mixture was extracted with three 30 ml portions of chloroform, and the combined extracts were washed with water, dried over Na$_2$SO$_4$ and evaporated to give an oily residue. Crystallization of the residue from methanol gave 202 mg (53% yield) of 2'-(ethoxycarbonyloxy)4,4',6'-trimethoxychalcone as pale yellow prisms; m.p. 107° C.

EXAMPLE 9

A solution of 2'-hydroxy-4,4',6'-trimethoxychalcone (1 g) and hydrochloride of nicotinoyl chloride (0.6 g) in 20 ml of pyridine was stirred at room temperature for 4 hours. After removal of the solvent followed by addition of saturated aqueous sodium bicarbonate (50 ml) to the residue, the mixture was extracted with ethyl acetate (100 ml). The extract was washed with water, dried over Na$_2$SO$_4$ and evaporated under reduced pressure to give an oily residue. Crystallization from methanol/hexane gave 1.1 g (83% yield) of 2',4,4'-trimethoxy-6'-(nicotinoyloxy)chalcone as pale yellow needles; m.p. 55°–60° C.

EXAMPLE 10

Thionyl chloride (0.46 ml) was added dropwise to a solution of 2'-hydroxy-4,4',6'-trimethoxychalcone (1 g) and pyrazinecarboxylic acid (592 mg) in 40 ml of pyridine, and the mixture was stirred at room temperature for 2 hours. Ice-water was added and the mixture was extracted with three 50 ml portions of ethyl acetate. The combined extracts were washed with water, dried over Na$_2$SO$_4$ and evaporated under reduced pressure to give a crystalline residue. Recrystallization from acetone gave 860 mg (64% yield) of 2',4,4'-trimethoxy-6'-(pyrrazinylcarbonyloxy)chalcone as pale yellow crystals; m.p. 163°–164° C.

EXAMPLE 11

Thionyl chloride (0.2 ml) was added to a well cooled solution of 2'-hydroxy-4,4',6'-trimethoxychalcone (0.2 g) and N-benzyloxycarbonyl-L-alanine in 5 ml of pyridine. After stirring at −15° to −20° C. for 3 hours followed by addition of 25 ml of ice-water, the mixture was extracted with 50 ml of chloroform. The extract was dried over Na$_2$SO$_4$ and evaporated under reduced pressure to give an oily residue. The residue was dissolved in a small amount of chloroform and applied onto a column of silica gel (1×30 cm). Elution with chloroform followed by removal of the solvent from the eluate gave 200 mg of pale yellow powder. Recrystallization from methanol/hexane yielded 150 mg of 2'-(N-benzyloxycarbonyl-L-alanyloxy)-4',4',6'-trimethoxychalcone as pale yellow needles; m.p. 163°–164° C. This material was then dissolved in 5 ml of acetic acid containing 25% hydrogen bromide. After being allowed to stand at room temperature for 20 minutes, the solution was lyophilized to give 120 mg of a powder which was washed with three 5 ml portions of chloroform, yielding 110 mg (20%) of 2'-(L-alanyloxy)-4',4',6'-trimethoxychalcone hydrobromide as yellow powder; m.p. 180°–185° C. (dec.)

EXAMPLE 12

Sodium hydride (76 mg of 60% purity) was added with stirring to an ice-cooled solution of 2'-hydroxy-4',6'-trimethoxychalcone (500 mg) in 20 ml of tetrahydrofuran. After 10 minutes, a solution of glutaric anhydride (218 mg) in 3 ml of tetrahydrofuran was added. The mixture was stirred at room temperature for 2 hours and evaporated under reduced pressure. The residue was dissolved in 50 ml of ethyl acetate, which was then extracted with 50 ml of 10% aqueous sodium carbonate. The extract was acidified with hydrochloric acid and shaken with 50 ml of chloroform. The chloroform extract was washed with water, dried over $Na_2SO_4$ and evaporated under reduced pressure. Crystallization of the residue from benzene gave 75 mg (11% yield) of 2'-(4-carboxybutanoyloxy)-4',4',6'-trimethoxychalcone as pale yellow crystals; m.p. 131°–132° C.

EXAMPLE 13

A mixture of 328 mg of 4-ethoxy-2'-hydroxy-4',6'-dimethoxychalcone, 0.3 ml of propionic anhydride and 20 mg of sodium propionate was heated at 130° C. for 2 hours. The resulting pale yellow oil was poured into about 70 ml of ice-water, and the mixture was extracted with two 70 ml portions of dichloromethane. The combined extracts were washed with water, dried over sodium sulfate and then evaporated.

Recrystallization of the residue from methanol yielded 267 mg (76%) of 4-ethoxy-2',4'-dimethoxy-6'-(propionyloxy)-chalcone as pale yellow crystals; m.p. 104.7° C.

EXAMPLE 14

In a manner analogous to that described in Example 13 except that 2'-hydroxy-4',6'-dimethoxy-4-propoxychalcone was used in place of 4-ethoxy-2'-hydroxy-4',6'-dimethoxychalcone, there was obtained 2',4'-dimethoxy-6'-(propionyloxy)-4-propoxychalcone; m.p. 102.5° C.

EXAMPLE 15

In a manner analogous to that described in Example 13 except that 2'-hydroxy-4',6'-dimethoxy-4-methylchalcone was used, there was obtained 2',4'-dimethoxy-4-methyl-6'-(propionyloxy)-chalcone; m.p. 156.0° C.

EXAMPLE 16

In a manner analogous to that described in Example 13 except that 2'-hydroxy-4',6'-dimethoxy-4-(methylthio)chalcone was used, there was obtained 2',4'-dimethoxy-4-(methylthio)-6'-(propionyloxy)-chalcone; m.p. 108.4° C.

EXAMPLE 17

In a manner analogous to that described in Example 13 except that 4-(allyloxy)-2'-hydroxy-4',6'-dimethoxychalcone was used, there was obtained 4-(allyloxy)-2',4'-dimethoxy-6'-(propionyloxy)-chalcone; m.p. 83.5° C.

EXAMPLE 18

In a manner analogous to that described in Example 13 except that 2',4,4'-triethoxy-6'-hydroxychalcone was used, there was obtained 2',4,4'-triethoxy-6'-(propionyloxy)-chalcone; m.p. 84.5° C.

EXAMPLE 19

In a manner analogous to that described in Example 13 except that 2'-hydroxy-4',6'-dimethoxychalcone was used, there was obtained 2',4'-dimethoxy-6'-(propionyloxy)-chalcone; m.p. 115.5°–117.0° C.

EXAMPLE 20

In a manner analogous to that described in Example 13 except that 4-chloro-2'-hydroxy-4',6'-dimethoxychalcone was used, there was obtained 4-chloro-2',4'-dimethoxy-6'-(propionyloxy)-chalcone; m.p. 136.0° C.

EXAMPLE 21

In a manner analogous to that described in Example 13 that 2'-ethoxy-6'-hydroxy-4,4'-dimethoxychalcone was used, there was obtained 2'-ethoxy-4,4'-dimethoxy-6'-(propionyloxy)-chalcone; m.p. 77.5° C. (benzene/hexane).

EXAMPLE 22

In a manner analogous to that described in Example 13 except that 2'-hydroxy-4',6'-dimethoxy-3-(2-thienyl)acrylophenone was used, there was obtained 2',4'-dimethoxy-6'-(propionyloxy)-3-(2-thienyl)-acrylophenone; m.p. 127.1° C.

EXAMPLE 23

In a manner analogous to that described in Example 13 except that 2'-hydroxy-4',6'-dimethoxy-3-(5-methyl-2-furyl)-acrylophenone was used, there was obtained 2',4'-dimethoxy-3-(5-methyl-2-furyl)-6'-(propionyloxy)-acrylophenone; m.p. 72.5° C.

EXAMPLE 24

In a manner analogous to that described in Example 13 except that 2'-hydroxy-4',6'-dimethoxy-3-(1-methylpyrrol-2-yl)-acrylophenone was used, there was obtained 2',4'-dimethoxy-3-(1-methylpyrrol-2-yl)-6'-(propionyloxy)-acrylophenone; m.p. 107.6° C.

EXAMPLE 25

In a manner analogous to that described in Example 13 except that 3-(2-furyl)-2'-hydroxy-4',6'-dimethoxyacrylophenone was used, there was obtained 3-(2-furyl)-2',4'-dimethoxy-6'-(propionyloxy)-acrylophenone; m.p. 93.6° C.

EXAMPLE 26

In a manner analogous to that described in Example 13 except that 2'-hydroxy-4',6'-dimethoxy-3,4-(methylenedioxy)-chalcone was used, there was obtained 2',4'-dimethoxy-3,4-(methylenedioxy)-6'-(propionyloxy)-chalcone; m.p. 134.5° C.

EXAMPLE 27

In a manner analogous to that described in Example 13 except that 2'-hydroxy-4,4'-dimethoxy-6'-propoxychalcone was used, there was obtained 4,4'-dimethoxy-2'-(propionyloxy)-6'-propoxychalcone;

$^1$H-nmr spectrum (in CDCl$_3$): δ0.89 (3H), 1.13(3H), 1.70(2H), 2.45(2H), 3.80(6H), 3.88(2H), 6.23(1H), 6.36(1H), 6.73(1H), 6.74(2H), 7.37(1H) and 7.46 ppm (2H).

EXAMPLE 28

In a manner analogous to that described in Example 13 except that 2'-hydroxy-6'-isopropoxy-4,4'-dimethoxychalcone was used, there was obtained 2'-isopropoxy-4,4'-dimethoxy-6'-(propionyloxy)chalcone;

$^1$H-nmr spectrum (in CDCl$_3$): δ1.22(9H), 2.44(2H), 3.80(6H), 4.52(1H), 6.23(1H), 6.33(1H), 6.83(1H), 6.84(2H), 7.37(1H) and 7.45 ppm (2H).

EXAMPLE 29

To a stirred solution containing 840 mg (4 mmoles) of 4'-ethoxy-2'-hydroxy-6'-methoxyacetophenone and 598 mg (4.4 mmoles) of anisaldehyde in 20 ml of ethanol were added 15 ml of 15% aqueous sodium hydroxide. After being stirred at room temperature for 3 days, the mixture was neutralized with 6N hydrochloric acid under cooling.

The resulting crystalline precipitate was collected by filtration, washed with water and then recrystallized from ethanol to give 945 mg (72%) of 4'-ethoxy-2'-hydroxy-4,6'-dimethoxychalcone as yellow needles; m.p. 122.0° C.

EXAMPLE 30

In a manner analogous to that described in Example 29 except that the corresponding acetophenones and aldehydes were used in place of 4'-ethoxy-2'-hydroxy-6'-methoxyacetophenone and anisaldehyde, respectively, there were obtained the following substituted acetophenones. Methanol was used as the solvent for recrystallization of all products with the exception that ethanol was used for recrystallization of 4,4'-diethoxy-2'-hydroxy-6'-methoxychalcone.

4,4'-diethoxy-2'-hydroxy-6'-methoxychalcone; m.p. 127.2° C.;

2'-hydroxy-3,4',6'-trimethoxychalcone; m.p. 97.6° C.;

2',4-diethoxy-6'-hydroxy-4'-methoxychalcone; m.p. 134.5° C.;

2'-hydroxy-3,4',5,6'-tetramethoxychalcone; m.p. 164.2° C.;

2,2'-dihydroxy-3,4',6'-trimethoxychalcone; m.p. 185.2° C.;

4'-ethoxy-2'-hydroxy-6'-methoxy-3-(5-methyl-2-furyl)-acrylophenone; m.p. 115.0° C.;

2'-ethoxy-6'-hydroxy-4'-methoxy-3-(5-methyl-2-furyl)-acrylophenone; m.p. 96.1° C.;

2',4'-diethoxy-6'-hydroxy-3-(5-methyl-2-furyl)-acrylophenone; m.p. 140.9° C.;

2',4'-diethoxy-6'-hydroxy-4-methoxychalcone; m.p. 137.0° C.;

2',3-dihydroxy-4,4',6'-trimethoxychalcone; m.p. 199.0° C.;

2'-hydroxy-3,4,4',6'-tetramethoxychalcone; m.p. 158.9° C.;

2'-hydroxy-2,4,4',6'-tetramethoxychalcone; m.p. 153.0° C.;

2'-hydroxy-2,3,4',6'-tetramethoxychalcone; m.p. 125.9° C.

EXAMPLE 31

To a stirred solution of 300 mg of 2'-hydroxy-4,4',6'-trimethoxychalcone in 12 ml of pyridine were added 65 mg of p-(dimethylamino)-pyridine and 165 mg of pivaloyl chloride. After being stirred at room temperature for 4 hours, the reaction mixture was poured into 30 ml of ice-water. The mixture was acidified with hydrochloric acid and then extracted with 50 ml of ethyl acetate. The ethyl acetate extract was successively washed with 0.2N hydrochloric acid, 10% aqueous sodium carbonate and water, dried over sodium sulfate and then evaporated to give 440 mg of 2',4,4'-trimethoxy-6'-(pivaloyloxy)-chalcone;

$^1$H-nmr (in CDCl$_3$): δ1.20(9H), 3.78(3H), 3.83(6H), 6.25(1H), 6.40(1H), 6.80(1H), 6.85(2H), 7.10(1H) and 7.45 ppm (2H).

What we claim is:

1. A method for treating an animal afflicted with a viral infection, which method comprises administering to such animal a compound of the formula:

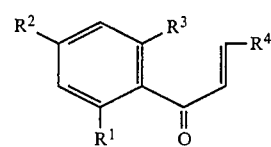

wherein

R$^1$ represents hydroxy; acyloxy derived from an aliphatic acid having 2–18 carbon atoms or derived from a heterocyclic carboxylic acid containing one or more nitrogen atoms; lower alkoxycarbonyloxy; aminoacyloxy or carboxyalkanoyloxy;

R$^2$ represents lower alkoxy;

R$^3$ represents hydrogen or lower alkoxy; and

R$^4$ represents phenyl which is unsubstituted or substituted by one or more substituents selected from the group consisting of lower alkyl, lower alkoxy, benzyloxy, allyloxy, alkylthio, dialkylamino, amino, cyano, hydroxy, halo and alkylenedioxy; or pyridyl, furyl, thienyl or pyrrolyl any of which is unsubstituted or substituted by lower alkyl, in an amount effective for inhibiting viral infections.

2. The method for treating an animal afflicted with a viral infection of claim 1 wherein the compound is 4'-ethoxy-2'-hydroxy-4-6'-dimethoxy chalcone.

3. A pharmaceutical composition comprising:

(a) a compound of the formula:

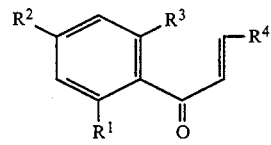

wherein

R$^1$ represents hydroxy, acyloxy derived from an aliphatic acid having 2–18 carbon atoms or derived from a heterocyclic carboxylic acid containing one or more nitrogen atoms; lower alkoxycarbonyloxy; aminoacyloxy or carboxyalkanoyloxy;

R$^2$ represents lower alkoxy;

$R^3$ represents lower alkoxy; and $R^4$ represents phenyl which is unsubstituted or substituted by one or more substituents selected from the group consisting of lower alkyl, lower alkoxy, benzyloxy, allyloxy, alkylthio, dialkylamino, amino, cyano, hydroxy, halo and alkylenedioxy; or pyridyl, furyl, thienyl or pyrrolyl any of which is unsubstituted or substituted by lower alkyl; and (b) a pharmaceutically acceptable carrier material, said composition being formulated in unit dosage form.

4. The composition of claim 3, wherein said composition is formulated in a systemic unit dosage form.

5. The composition of claim 3, wherein said composition is formulated in an oral unit dosage form.

6. The composition of claim 5 wherein the oral dosage form is selected from the group consisting of tablets, capsules, pills, powders, granules, solutions, suspensions, syrups and elixers.

7. The composition of claim 4 comprising about 100 to about 2,000 mg of compound I.

8. The composition of claim 3 wherein $R^{1'}$ is hydroxy and $R^{2'}$ and $R^{3'}$ are each lower alkoxy and $R^{4'}$ is a phenyl having a lower alkoxy substituent.

9. The composition of claim 3 wherein the compound is 4'-ethoxy-2'-hydroxy-4-6'-dimethoxy chalcone.

10. The composition of claim 3, wherein said composition is formulated in topical unit dosage form.

11. The composition of claim 10, wherein the topical unit dosage form is selected from the group consisting of solutions, emulsions, micronized powders, ointments, gargles, troches and aerosoles.

12. The composition of claim 10 comprising 0.1 to 100 $\mu g/cm^2$ of compound I.

13. The composition of claim 10 wherein $R^{1'}$ is hydroxy and $R^{2'}$ and $R^{3'}$ are each lower alkoxy and $R^{4'}$ is a phenyl having a lower alkoxy substituent.

14. The composition of claim 10 wherein the compound is 4'-ethoxy-2'hydroxy-4-6'-dimethoxy chalcone.

15. The composition of claim 10 wherein compound I is present in an amount which is effective against viruses.

* * * * *